United States Patent
Luo et al.

(10) Patent No.: US 10,610,809 B2
(45) Date of Patent: Apr. 7, 2020

(54) PROCESS USING AN INTEGRATED COALESCING SYSTEM FOR SEPARATING DISPERSED IONIC LIQUID FROM LIQUID HYDROCARBON

(71) Applicant: Chevron U.S.A. Inc., San Ramon, CA (US)

(72) Inventors: Huping Luo, Richmond, CA (US); Hye-Kyung Cho Timken, Albany, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 280 days.

(21) Appl. No.: 15/926,088

(22) Filed: Mar. 20, 2018

(65) Prior Publication Data

US 2018/0207552 A1  Jul. 26, 2018

Related U.S. Application Data

(62) Division of application No. 15/251,640, filed on Aug. 30, 2016, now Pat. No. 9,956,504.

(51) Int. Cl.
*B01D 17/04* (2006.01)
*B01D 17/02* (2006.01)
(Continued)

(52) U.S. Cl.
CPC ....... *B01D 17/045* (2013.01); *B01D 17/0214* (2013.01); *B01D 17/10* (2013.01);
(Continued)

(58) Field of Classification Search
CPC .. B01D 17/0214; B01D 17/045; B01D 17/10; C10G 33/06; C10G 31/00; C10G 1/04;
(Continued)

(56) References Cited

U.S. PATENT DOCUMENTS

| 8,067,656 B2 | 11/2011 | Luo et al. |
| 8,198,499 B2 | 6/2012 | Luo et al. |

(Continued)

FOREIGN PATENT DOCUMENTS

| CN | 102021019 A | 4/2011 |
| CN | 203247096 U | 10/2013 |

(Continued)

*Primary Examiner* — John Kim

(57) ABSTRACT

A process is provided for separating an ionic liquid from a liquid hydrocarbon, using an integrated coalescing system. The integrated coalescing system for separating ionic liquid from a liquid hydrocarbon may comprise:

a. a bulk settler,
that separates an emulsion comprising the dispersed ionic liquid with a wide range of droplet sizes into a clean ionic liquid phase and a separated liquid hydrocarbon phase comprising retained droplets;

b. a pre-coalescer that receives the separated liquid hydrocarbon phase, separates out solid particles from the separated liquid hydrocarbon phase, and begins to form coalesced droplets of the retained droplets; and c. a coalescer that receives an effluent from the pre-coalescer, wherein the at least one coalescer comprises multiple layers of media having a fine pore size, and produces a clean hydrocarbon stream that is essentially free of the dispersed ionic liquid and additional amounts of the clean ionic liquid phase.

14 Claims, 7 Drawing Sheets

(51) Int. Cl.
  *B01D 17/00*  (2006.01)
  *C07C 7/00*  (2006.01)
  *C10G 33/06*  (2006.01)
  *C10G 31/00*  (2006.01)

(52) U.S. Cl.
  CPC ............ *C07C 7/00* (2013.01); *C07C 7/005* (2013.01); *C10G 31/00* (2013.01); *C10G 33/06* (2013.01)

(58) Field of Classification Search
  CPC ........... C10G 1/002; C07C 7/00; C07C 7/005; C07C 9/15
  See application file for complete search history.

(56) References Cited

U.S. PATENT DOCUMENTS

| | | |
|---|---|---|
| 8,704,018 B2 | 4/2014 | Timken et al. |
| 8,795,515 B2 | 8/2014 | Zhan et al. |
| 8,920,755 B2 | 12/2014 | Cleverdon et al. |
| 8,969,645 B2 | 3/2015 | Zhan et al. |
| 9,095,789 B2 | 8/2015 | Pfeiffer et al. |
| 9,254,450 B2 | 2/2016 | Timken et al. |
| 2010/0130800 A1 | 5/2010 | Luo et al. |
| 2011/0155632 A1 | 6/2011 | Timken et al. |
| 2012/0292252 A1 | 11/2012 | Chase et al. |
| 2013/0066130 A1 | 3/2013 | Luo et al. |
| 2014/0039231 A1 | 2/2014 | Timken et al. |
| 2014/0357915 A1 | 12/2014 | Lacheen |
| 2016/0168055 A1 | 6/2016 | Buchbinder et al. |
| 2016/0168058 A1 | 6/2016 | Detrick et al. |

FOREIGN PATENT DOCUMENTS

| | | |
|---|---|---|
| WO | 2011015662 A2 | 2/2011 |
| WO | 2011015664 | 2/2011 |
| WO | 2014011574 | 1/2014 |
| WO | 2016094183 | 6/2016 |

PROCESS USING AN INTEGRATED COALESCING SYSTEM FOR SEPARATING DISPERSED IONIC LIQUID FROM LIQUID HYDROCARBON

This application is a divisional of U.S. patent application Ser. No. 15/251,640, published as US201800562123A1, filed Aug. 30, 2016, now U.S. Pat. No. 9,956,504; and herein incorporated in its entirety.

TECHNICAL FIELD

This application is directed to improved systems and processes for separating dispersed ionic liquids from liquid hydrocarbons.

SUMMARY

This application provides an integrated coalescing system for separating a dispersed ionic liquid from a liquid hydrocarbon, comprising:

a. at least one bulk settler,
that receives an emulsion comprising the dispersed ionic liquid with a wide range of droplet sizes ranging from small droplets less than 20 microns to large droplets greater than 500 microns, and
that separates the emulsion into a clean ionic liquid phase, that is essentially free of the liquid hydrocarbon, and into a separated liquid hydrocarbon phase comprising retained ionic liquid droplets;

b. at least one pre-coalescer connected to the at least one bulk settler that receives the separated liquid hydrocarbon phase, separates out solid particles from the separated liquid hydrocarbon phase, and begins to form coalesced droplets of the retained ionic liquid droplets; and c. at least one coalescer that is fluidly connected to the at least one pre-coalescer and receives an effluent from the at least one pre-coalescer, wherein the at least one coalescer comprises multiple layers of media having a fine pore size of 20 microns or less, and produces a clean hydrocarbon stream that is essentially free of the dispersed ionic liquid and additional amounts of the clean ionic liquid phase.

This application also provides a process for separating an ionic liquid from a liquid hydrocarbon, comprising:

a. settling an emulsion of the ionic liquid and the liquid hydrocarbon, wherein the emulsion comprises a dispersed ionic liquid with a wide range of droplet sizes, ranging from small droplets less than 20 microns to large droplets greater than 500 microns, to separate a clean ionic liquid phase that is free of the liquid hydrocarbon from a separated liquid hydrocarbon phase comprising retained ionic liquid droplets;

b. pre-coalescing the separated liquid hydrocarbon phase in at least one pre-coalescer that removes any particles and begins to form coalesced droplets of the dispersed ionic liquid;

c. coalescing an effluent from the at least one pre-coalescer in at least one coalescer comprising multiple layers of media having a fine pore size of 20 microns or less to produce a clean hydrocarbon stream that is essentially free of the dispersed ionic liquid and produces additional amounts of the clean ionic liquid phase.

The present invention may suitably comprise, consist of, or consist essentially of, the elements in the claims, as described herein.

GLOSSARY

"Dispersed" refers to a distribution (as fine droplets) more or less evenly throughout a medium.

"Ionic Liquid" refers to materials consisting entirely of ions that is a salt in which the ions are poorly coordinated, which results in the salt being liquid below 100° C., or even at room temperature "Acidic ionic liquid" refers to ionic liquids consisting entirely of ions, that can donate a proton or accept an electron pair in reactions, and that are liquid below 100° C.

"Emulsion" refers to a colloid of two or more immiscible liquids where one liquid contains a dispersion of the other liquids. In the context of this disclosure the ionic liquid will form droplets and disperse throughout a hydrocarbon.

"Liquid" refers to a phase of matter in which atoms or molecules can move freely while remaining in contact with one another. A liquid takes the shape of its container, and is unlike a gas or a solid.

"Bulk settler" refers to an apparatus that separates a dispersed phase from an emulsion using the different density of the liquids being separated.

"Predominantly" refers to greater than 50 wt %, such as from greater than 50 wt % up to 100 wt %, in the context of this disclosure.

"Essentially" refers to from 90 wt % to 100 wt % in the context of this disclosure.

"Periodic Table" refers to the version of the IUPAC Periodic Table of the Elements dated Jun. 22, 2007, and the numbering scheme for the Periodic Table Groups is as described in Chemical And Engineering News, 63(5), 27 (1985).

"Hydrophilic" refers to a property of a substance to have a tendency to mix with, dissolve in, or be wetted by water.

"Hydrophobic" refers to a property of a substance to repel water. Hydrophobic molecules tend to be nonpolar molecules and group together.

"Fiberglass" is a type of fiber-reinforced plastic where the reinforcement fiber is specifically glass fiber. In the context of this disclosure, fiberglass refers to the complete glass-fiber-reinforced composite material, rather than only to the glass fiber within it.

"Turbidity" is the cloudiness or haziness of a fluid caused by large numbers of individual particles or droplets that are generally invisible to the naked eye. Turbidity can be measured with an instrument called a nephelometer, with a detector set up to the side of a light beam. More light reaches the detector if there are lots of small droplets scattering the source beam than if there are few. The units of turbidity from a calibrated nephelometer are called Nephelometric Turbidity Units (NTU).

DETAILED DESCRIPTION

Bulk Settler

The bulk settler receives the emulsion comprising the dispersed ionic liquid and separates the emulsion into a clean ionic liquid phase and a separated liquid hydrocarbon phase comprising retained ionic liquid droplets. Examples of bulk settlers include: centrifuges, gravity settlers, membrane-assisted settlers, impingement separators, inclined plate settlers, scroll centrifuges, settler tanks, and cyclone separators.

In one embodiment, the bulk settler uses gravity to separate the emulsion. In one embodiment, to enhance its performance, the bulk settler may comprise one or more coarse coalescing pads, such as structured packing, parallel plates or knitted mesh, which can be made from metal or nonmetallic materials that are compatible with the emulsion.

In one embodiment, the bulk settler is configured to predominantly, but not completely, separate the dispersed ionic liquid from the emulsion. In one embodiment, the emulsion remains in the bulk settler for 0.10 to 10 hours.

In one embodiment, the bulk settler is sized to accept from greater than 50 vol % to 100 vol % of the effluent from a hydrocarbon conversion reactor that forms the emulsion. In another embodiment, the bulk settler is sized to receive all, or essentially all, of the effluent from the hydrocarbon conversion reactor that forms the emulsion.

Figure 6:
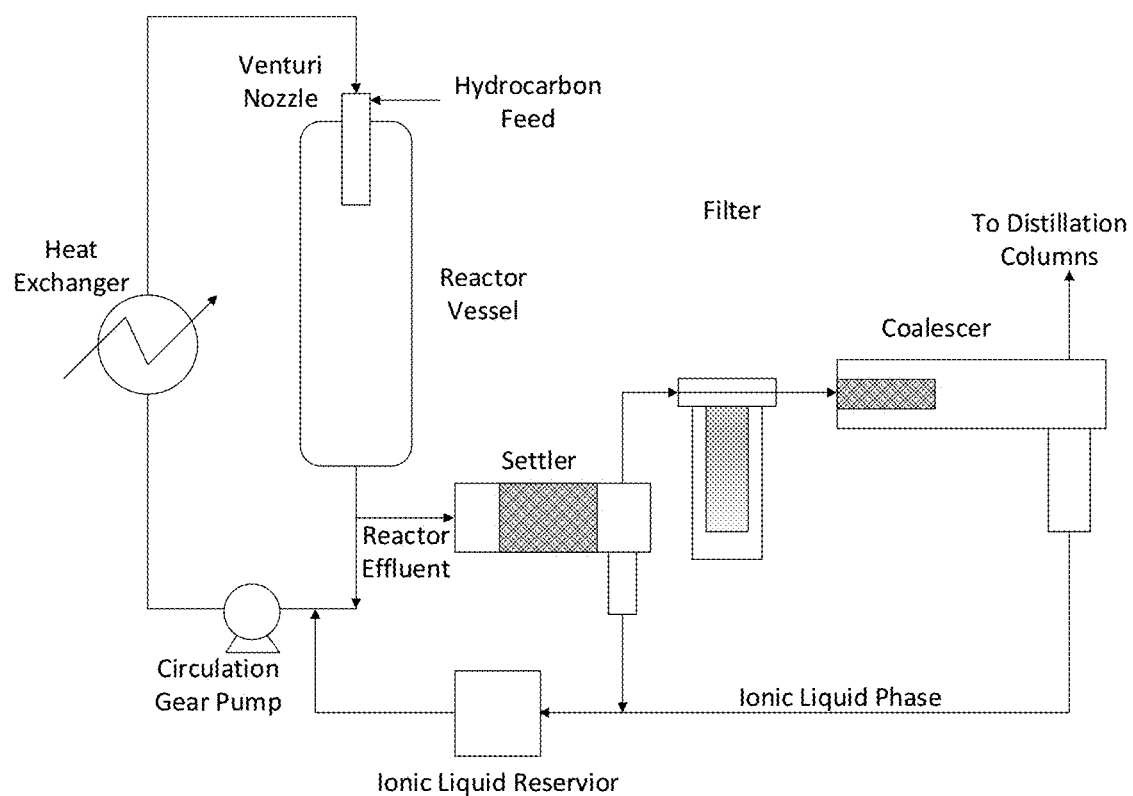
FIG. 6 is a schematic diagram of a pilot plant with an integrated coalescing system for separating an ionic liquid from a liquid hydrocarbon.

In one embodiment, the bulk settler is fluidly connected to a hydrocarbon conversion reactor that produces the emulsion, and the clean ionic liquid phase is fed to an inlet of the hydrocarbon conversion. This embodiment is shown in FIG. 6.

The settling step, such as in the bulk settler, separates the emulsion into a clean ionic liquid phase that is essentially free of the liquid hydrocarbon. By "essentially free of the liquid hydrocarbon" refers to a condition wherein the clean ionic liquid phase contains no hydrocarbon droplets, however, the clean ionic liquid phase may still contain small amounts of hydrocarbon that is completely dissolved in the clean ionic liquid phase. The small amounts of the liquid hydrocarbon that can be dissolved in the clean ionic liquid can be from zero to 5 wt %. Any hydrocarbon that is dissolved into the clean ionic liquid phase will not be separated out by the settling and coalescing.

In one embodiment, the clean ionic liquid phase may retain less than 5 wt % of the liquid hydrocarbon that has dissolved into the ionic liquid phase.

The clean ionic liquid phase can be sent to an ionic liquid reservoir, or a portion thereof can be sent to a regeneration apparatus. The clean ionic liquid phase can be suitable for use in a hydrocarbon conversion reactor. This clean ionic liquid phase can be combined with an additional ionic liquid phase produced in the coalescer and they can be circulated together to the hydrocarbon conversion reactor.

Hydrocarbon Conversion Reactor

Examples of hydrocarbon conversion reactors include continuously stirred tank reactors, fixed bed reactors, nozzles, motionless mixers, and pressure vessels. Examples of hydrocarbon conversion processes performed in the hydrocarbon conversion reactor include paraffin alkylation, olefin dimerization, olefin oligomerization, concurrent alkylation and oligomerization, isomerization, and aromatic alkylation. In one embodiment, the hydrocarbon conversion reactor can make gasoline, middle distillate, base oil, or petrochemical components.

In one embodiment, the hydrocarbon conversion reactor makes the emulsion. In one embodiment the hydrocarbon conversion reactor is a nozzle reactor comprising one or more Venturi nozzles. In another embodiment, the hydrocarbon conversion reactor comprises one or more high shear mixers.

Emulsion

The emulsion comprises a dispersed ionic liquid phase in a hydrocarbon continuous phase. The emulsion comprising the dispersed ionic liquid has a wide range of droplet sizes, ranging from small droplets less than 20 microns to large droplets greater than 500 microns. Examples of droplet size distributions that can be used include those shown in FIGS. 2 and 3, which have droplet size distributions from less than 1 micron up to about 1000 microns.

In one embodiment, the emulsion comprises the small droplets of the ionic liquid that are less than 10 microns. The emulsion comprises the dispersed ionic liquid in a liquid hydrocarbon. In one embodiment, the liquid hydrocarbon is a liquid at ambient temperature and pressure. In one embodiment the liquid hydrocarbon may comprise one or more of an alkylate gasoline, a base oil, a middle distillate, or a chemical intermediate.

In one embodiment, the emulsion contains 1-30 vol % of the dispersed ionic liquid. In another embodiment, the emulsion contains 1-10 vol % of the dispersed ionic liquid. In another further embodiment, the emulsion contains 1-3 vol % of the dispersed ionic liquid.

In one embodiment, the emulsion is produced by feeding a hydrocarbon and an ionic liquid separately into one or more Venturi nozzles. In the Venturi nozzles, the ionic liquid is mixed intimately with the hydrocarbon and is dispersed into fine droplets. In another embodiment, the emulsion is produced by mixers, such as high shear mixers.

Acidic Ionic Liquid

In one embodiment, the dispersed ionic liquid is an acidic ionic liquid. Examples of acidic ionic liquid catalysts and their use for alkylation of paraffins with olefins are taught, for example, in U.S. Pat. Nos. 7,432,408 and 7,432,409, 7,285,698, and U.S. patent application Ser. No. 12/184,069, filed Jul. 31, 2008. In one embodiment, the acidic ionic liquid is a composite ionic liquid catalyst, wherein the cations come from a hydrohalide of an alkyl-containing amine or pyridine, and the anions are composite coordinate anions coming from two or more metal compounds.

The most common acidic ionic liquids are those prepared from organic-based cations and inorganic or organic anions. The acidic ionic liquid is composed of at least two components which form a complex. The acidic ionic liquid comprises a first component and a second component. The first component of the acidic ionic liquid will typically comprise a Lewis acid compound selected from components such as Lewis acid compounds of Group 13 metals, including aluminum halides, alkyl aluminum dihalides, gallium halide, and alkyl gallium halide (see the Periodic Table, which defines the elements that are Group 13 metals). Other Lewis acid compounds besides those of Group 13 metals may also be used. In one embodiment the first component is aluminum halide or alkyl aluminum dihalide. For example, aluminum trichloride ($AlCl_3$) may be used as the first component for preparing the ionic liquid catalyst. In one embodiment, the alkyl aluminum dihalides that can be used can have the general formula $Al_2X_4R_2$, where each X represents a halogen, selected for example from chlorine and bromine, each R represents a hydrocarbyl group comprising 1 to 12 atoms of carbon, aromatic or aliphatic, with a branched or a linear chain. Examples of alkyl aluminum dihalides include dichloromethylaluminum, dibromomethylaluminum, dichloroethylaluminum, dibromoethylaluminum, dichloro n-hexylaluminum, dichloroisobutylaluminum, either used separately or combined.

The second component making up the acidic ionic liquid can be an organic salt or mixture of salts. These salts may be characterized by the general formula Q+A−, wherein Q+ is an ammonium, phosphonium, boronium, oxonium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $Al_2Cl_7^-$, $Al_3Cl_{10}^-$, $GaCl_4^-$, $Ga_2Cl_7^-$, $Ga_3Cl_{10}^-$, $AsF_6^-$, $TaF_6^-$, $CuCl_2^-$, $FeCl_3^-$, $AlBr_4^-$, $Al_2Br_7^-$, $Al_3Br_{10}^-$, $SO_3CF_3^-$, and 3-sulfurtrioxyphenyl.

In one embodiment the second component is selected from those having quaternary ammonium halides containing one or more alkyl moieties having from about 1 to about 9 carbon atoms, such as, for example, trimethylammonium hydrochloride, methyltributylammonium, 1-butyl pyridinium, or alkyl substituted imidazolium halides, such as for example, 1-ethyl-3-methyl-imidazolium chloride.

In one embodiment, the acidic ionic liquid comprises a monovalent cation selected from the group consisting of a pyridinium ion, an imidazolium ion, a pyridazinium ion, a pyrazolium ion, an imidazolinium ion, a imidazolidinium ion, an ammonium ion, a phosphonium ion, and mixtures thereof. Examples of possible cations (Q+) include a butylethylimidazolium cation [beim], a butylmethylimidazolium cation [bmim], butyldimethylimidazolium cation [bmmim], decaethylimidazolium cation [dceim], a decamethylimidazolium cation [dcmim], a diethylimidazolium cation [eeim], a dimethylimidazolium cation [mmim], an ethyl-2,4-dimethylimidazolium cation [e-2,4-mmim], an ethyldimethylimidazolium cation [emmim], an ethylimidazolium cation [eim], an ethylmethylimidazolium [emim] cation, an ethylpropylimidazolium cation [epim], an ethoxyethylmethylimidazolium cation [etO-emim], an ethoxydimethylimidazolium cation [etO-mmim], a hexadecylmethylimidazolium cation [hexadmim], a heptylmethylimidazolium cation [hpmim], a hexaethylimidazolium cation [hxeim], a hexamethylimidazolium cation [hxmim], a hexadimethylimidazolium cation [hxmmim], a methoxyethylmethylimidazolium cation [meO-emim], a methoxypropylmethylimidazolium cation [meO-prmim], a methylimidazolium cation [mim], dimethylimidazolium cation [mmim], a methylnonylimidazolium cation [mnim], a methylpropylimidazolium cation [mpim], an octadecylmethylimidazolium cation [octadmim], a hydroxyethylmethylimidazolium cation [OH-emim], a hydroxyoctylmethylimidazolium cation [OH-omim], a hydroxylpropylmethylimidazolium cation [OH-prmim], an octylmethylimidazolium cation [omim], an octyldimethylimidazolium cation [ommim], a phenylethylmethylimidazolium cation [ph-emim], a phenylmethylimidazolium cation [ph-mim], a phenyldimethylimidazolium cation [ph-mmim], a pentylmethylimidazolium cation [pnmim], a propylmethylimidazolium cation [prmim], a 1-butyl-2-methylpyridinium cation[1-b-2-mpy], 1-butyl-3-methylpyridinium cation[1-b-3-mpy], a butylmethylpyridinium [bmpy] cation, a 1-butyl-4-dimethylacetylpyridinium cation [1-b-4-DMApy], a 1-butyl-4-35 methylpyridinium cation[1-b-4-mpy], a 1-ethyl-2-methylpyridinium cation[1-e-2-mpy], a 1-ethyl-3-methylpyridinium cation[1-e-3-mpy], a 1-ethyl-4-dimethylacetylpyridinium cation[1-e-4-DMApy], a 1-ethyl-4-methylpyridinium cation[1-e-4-mpy], a 1-hexyl-5 4dimethylacetylpyridinium cation[1-hx-4-DMApy], a 1-hexyl-4-methylpyridinium cation[1-hx-4-mpy], a 1-octyl-3-methylpyridinium cation[1-o-3-mpy], a 1-octyl-4-methylpyridinium cation[1-o-4-mp y], a 1-propyl-3-methylpyridinium cation[1-pr-3-mpy], a 1-propyl-4-methylpyridinium cation[1-pr-4-mpy], a butylpyridinium cation [bpy], an ethylpyridinium cation [epy], a heptylpyridinium cation [hppy], a hexylpyridinium cation [hxpy], a hydroxypropylpyridinium cation [OH-prpy], an octylpyridinium cation [opy], a pentylpyridinium cation [pnpy], a propylpyridinium cation [prpy], a butylmethylpyrrolidinium cation [bmpyr], a butylpyrrolidinium cation [bpyr], a hexylmethylpyrrolidinium cation [hxmpyr], a hexylpyrrolidinium cation [hxpyr], an octylmethylpyrrolidinium cation [ompyr], an octylpyrrolidinium cation [opyr], a propylmethylpyrrolidinium cation [prmpyr], a butylammonium cation [b-N], a tributylammonium cation [bbb-N], a tetrabutylammonium cation [bbbb-N], a butylethyldimethylammonium cation [bemm-N], a butyltrimethylammonium cation [bmmm-N], a N,N,N-trimethylethanolammonium cation [choline], an ethylammonium cation [e-N], a diethylammonium cation [ee-N], a tetraethylammonium cation [eeee-N], a tetraheptylammonium cation [hphphphp-N], a tetrahexylammonium cation [hxhxhxhx-N], a methylammonium cation [m-N], a dimethylammonium cation [mm-N], a tetramethylammonium cation [mmmm-N], an ammonium cation [N], a butyldimethylethanolammonium cation [OHe-bmm-N], a dimethylethanolammonium cation [OHe-mm-N], an ethanolammonium cation [OHe—N], an ethyldimethylethanolammonium cation [OHe-emm-N], a tetrapentylammonium cation [pnpnpnpn-N], a tetrapropylammonium cation [prprprpr-N], a tetrabutylphosphonium cation [bbbb-P], a tributyloctylphosphonium cation [bbbo-P], or combinations thereof.

In one embodiment, the second component is selected from those having quaternary phosphonium halides containing one or more alkyl moieties having from 1 to 12 carbon atoms, such as, for example, trialkyphosphonium hydrochloride, tetraalkylphosphonium chlorides, and methyltrialkyphosphonium halide.

In one embodiment, the acidic ionic liquid comprises an unsubstituted or partly alkylated ammonium ion.

In one embodiment, the acidic ionic liquid is chloroaluminate or a bromoaluminate. In one embodiment the acidic ionic liquid is a quaternary ammonium chloroaluminate ionic liquid having the general formula RR' R" N H+$Al_2Cl_7^-$, wherein R, R', and R" are alkyl groups containing 1 to 12 carbons. Examples of quaternary ammonium chloroaluminate ionic liquids are an N-alkyl-pyridinium chloroaluminate, an N-alkyl-alkylpyridinium chloroaluminate, a pyridinium hydrogen chloroaluminate, an alkyl pyridinium hydrogen chloroaluminate, a di alkyl-imidazolium chloroaluminate, a tetra-alkyl-ammonium chloroaluminate, a tri-alkyl-ammonium hydrogen chloroaluminate, or a mixture thereof.

The presence of the first component should give the acidic ionic liquid a Lewis or Franklin acidic character. Generally, the greater the mole ratio of the first component to the second component, the greater is the acidity of the acidic ionic liquid.

For example, a typical reaction mixture to prepare n-butyl pyridinium chloroaluminate ionic liquid is shown below:

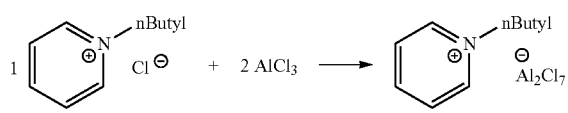

In one embodiment, the acidic ionic liquid utilizes a co-catalyst to provide enhanced or improved alkylation activity. Examples of co-catalysts include alkyl halide or hydrogen halide. A co-catalyst can comprise, for example, anhydrous HCl or organic chloride (see, e.g., U.S. Pat. No. 7,495,144 to Elomari, and U.S. Pat. No. 7,531,707 to Harris et al.). When organic chloride is used as the co-catalyst with the acidic ionic liquid, HCl may be formed in situ in the apparatus either during the alkylating or during post-processing of the output of the alkylating. In one embodiment, the alkylating with the acidic ionic liquid is conducted in the presence of a hydrogen halide, e.g., HCl.

The alkyl halides that may be used include alkyl bromides, alkyl chlorides and alkyl iodides. Such alkyl halides include but are not limited to isopentyl halides, isobutyl halides, t-butyl halides, n-butyl halides, propyl halides, and ethyl halides. Alkyl chloride versions of these alkyl halides can be preferable when chloroaluminate ionic liquids are used. Other alkyl chlorides or alkyl halides having from 1 to 8 carbon atoms can be also used. The alkyl halides may be used alone or in combination.

When used, the alkyl halide or hydrogen halide co-catalysts are used in catalytic amounts. In one embodiment, the amounts of the alkyl halides or hydrogen halide should be kept at low concentrations and not exceed the molar concentration of the $AlCl_3$ in the acidic ionic liquid. For example, the amounts of the alkyl halides or hydrogen halide used may range from 0.05 mol %-100 mol % of the Lewis acid $AlCl_3$ in the acidic ionic liquid in order to keep the acidity of the acidic ionic liquid catalyst at the desired performing capacity.

In one embodiment, the acidic alkylation catalyst comprises an ionic liquid catalyst and a Brønsted acid. In this embodiment, the Brønsted acid acts as a promoter or co-catalyst. Examples of Brønsted acids are sulfuric acid, HCl, HBr, HF, phosphoric acid, HI, etc. Other strong acids that are proton donors can also be suitable Brønsted acids. In one embodiment, the Brønsted acid is produced internally within the process by the conversion of an alkyl halide into the corresponding hydrogen halide.

Pre-Coalescer

The integrated coalescing system additionally comprises at least one pre-coalescer connected to the at least one bulk settler. The pre-coalescer receives the separated liquid hydrocarbon phase that still comprises retained ionic liquid droplets. The pre-coalescer separates out solid particles, from the separated liquid hydrocarbon phase, that could potentially foul the downstream coalescer. The pre-coalescer also begins to form coalesced droplets of the retained ionic liquid droplets. The pre-coalescer can function as a preconditioner and allows more efficient separation in a subsequent fluidly-connected coalescer. The pre-coalescing of the separated liquid hydrocarbon phase in the at least one pre-coalescer can remove solid particles and begin to form coalesced droplets of the dispersed ionic liquid.

In one embodiment, the pre-coalescer is selected to comprise a medium with a pore size smaller than the pore size of the media in the downstream coalescer, allowing the removal of any solid particles that could potentially foul the downstream coalescer. In one embodiment, the solid particles removed by the pre-coalescer are contaminants in one or both of the ionic liquid phase and the hydrocarbon phase. The contaminants may be one or more of corrosion products, partially hydrolyzed ionic liquid, and other contaminants carried from upstream processes. In one embodiment, the solid particles are not particles that are formed in the hydrocarbon conversion reactor. In one embodiment, no separated ionic liquid phase is collected from the pre-coalescer. In one embodiment, the pre-coalescer has one outlet.

In one embodiment, the pre-coalescer has a medium with a pore size less than 50 microns, such as from 1 to 25 microns. In one embodiment, the pre-coalescer comprises a medium made from fiber glass, wool, resins, polymers or fine metal mesh. In one embodiment, the medium used in the pre-coalescer is compatible with the separated liquid hydrocarbon phase and the retained ionic liquid droplets.

In one embodiment, the pre-coalescer comprises a filter. In one embodiment the filter has a pore size from 2 to 20 microns, such as from 3 to 15 microns, or from 5 to 12 microns. The pre-coalescer can effectively remove solid particles from the separated liquid hydrocarbon phase and prevent fouling of the downstream coalescer, therefore significantly extending the life of the downstream coalescer. In one embodiment, the pre-coalescer is configured to target the removal of solid particles that could foul the downstream coalescer. For example, the pre-coalescer can comprise a filter that removes solid particles greater than or equal to 1 micron, such as from 1 to 3000 microns, greater than 5 microns, or greater than 10 microns.

In one embodiment, the effluent from the pre-coalescer is passed directly through the outlet of the pre-coalescer into an inlet of a coalescer that is fluidly connected to the pre-coalescer.

Coalescer

The integrated coalescing system additionally comprises at least one coalescer that is fluidly connected to the at least one pre-coalescer. The coalescer receives an effluent from the pre-coalescer. The coalescer comprises multiple layers of media having a fine pore size of 20 microns or less. The coalescer produces both a clean hydrocarbon stream that is essentially free of the dispersed ionic liquid and also additional amounts of the clean ionic liquid phase.

In one embodiment, the multiple layers of media can be arranged to have alternating hydrophilic surface properties and hydrophobic surface properties. Examples of media having hydrophilic surface properties include various metals, including metal alloys. In one embodiment, the metal media provides structural support for the other media in the coalescer. In a sub-embodiment, one or more layers of media with the hydrophilic surface properties in the at least one coalescer comprise a metal.

In one embodiment, the multiple layers of media additionally comprise a hydrophilic media comprising a metal Examples of hydrophilic media having the hydrophilic surface properties include high alloy metals such as stainless steel, high nickel alloys, and titanium alloys. Stainless steel is a steel alloy with a minimum of 10.5% chromium content by mass. Stainless steel does not readily corrode, rust or stain with water as ordinary steel does. There are different grades and surface finishes of stainless steel to suit the environment the alloy must endure. Stainless steel can be used where both the properties of steel and corrosion resistance are desired.

Different metals and metal alloys are defined by their elemental composition. They can be defined by ASTM standards or by the unified numbering system. The unified numbering system (UNS) is an alloy designation system widely accepted in North America. It consists of a prefix letter and five digits designating a material composition. For example, a prefix of S indicates stainless steel alloys, C indicates copper, brass, or bronze alloys, N indicates nickel and nickel alloys, R indicates refractory alloys, T indicates tool steels, and so on. The first 3 digits often match older 3-digit numbering systems, while the last 2 digits indicate more modern variations. ASTM E527-12 is the Standard Practice for Numbering Metals and Alloys in the Unified Numbering System (UNS). The UNS is managed jointly by the ASTM International and SAE International. A UNS number alone does not constitute a full material specification because it establishes no requirements for material properties, heat treatment, form, or quality.

High alloy metals can include one or more of the following UNS numbers: N08020, S30403, S31603, S31703, N08904, 531254, N08367, N08225, S44660, S31803, S32205, S32750, N04400, N10276, N06022, N10665, R50400, R52400, R53400, and R52402.

In one embodiment, the high alloy metal is one that is especially cost effective as well as resistant to corrosion in the presence of the coalesced droplets of the dispersed ionic liquid. One example of a suitable high alloy metal comprises: from 15.1 to 49 wt % nickel, from 2.3 to 10 wt % molybdenum, from 0.00 to 2.95 wt % copper, and from 20 to 59 wt % iron; wherein the metal alloy exhibits a corrosion rate less than 0.07 mm/year when performing the coalescing. These metal alloys are described in US20160067668A1. In one embodiment, the high alloy metal has a UNS number selected from the group consisting of N08904, S31254, N08367, and N08225.

In one embodiment, the multiple layers of media comprise a hydrophobic media having the fine pore size of 10 microns or less that coalesces droplets in the emulsion and produces a clean liquid hydrocarbon stream. In one embodiment, the multiple layers of media comprise a hydrophobic media, and the hydrophobic media has the fine pore size of 20 microns or less, such as 1 to 10 microns. The hydrophobic media efficiently coalesces droplets in the emulsion and produces the clean hydrocarbon stream. In one embodiment, the hydrophobic media has the fine pore size of 10 microns or less.

In one embodiment, the clean hydrocarbon stream is visually crystal clear when optically observed without any magnification. In one embodiment, the clean hydrocarbon stream can have excellent low turbidity, such as from 0.1 to less than 10 NTU, or from 0.1 to less than 5 NTU. In one embodiment, the clean hydrocarbon stream comprises less than 50 ppmv of the dispersed ionic liquid, such as from zero to 20 ppmv. The amount of the dispersed ionic liquid in the clean hydrocarbon stream can be measured by chemical analysis.

Examples of hydrophobic media having hydrophobic surface properties include materials made from hydrocarbons, including engineered polymers. Examples of engineered polymers include fiberglass, epoxy resins, polyester resins, vinylesters, thermoplastic resins, acrylic/phenolic resin, nylon, or combinations thereof. In one embodiment, the media having hydrophobic surface properties comprise a fiberglass. In one embodiment, the media having hydrophobic surface properties comprises a polyester material. Other examples of engineered polymers include polybutylene terephthalate (PBT), polyamide materials, fluoropolymer, polyolefin or a media obtained by treating a fibrous engineered polymer with an agent comprising fluorine functionalities.

In one embodiment, the multiple layers of media comprises at least one layer of media material that remains relatively non-wettable by the retained ionic liquid droplets in the effluent from the pre-coalescer. Engineered polymers, such as those described previously can remain relatively non-wettable by the retained ionic liquid droplets in the effluent from the pre-coalescer.

In one embodiment, the coalescer is made without any metals.

In one embodiment, the media having hydrophobic surface properties comprises a fiberglass. The glass fibers in the fiberglass may be randomly arranged, flattened into a sheet (called a chopped strand mat), or woven into a fabric. A plastic matrix of the fiberglass may be a thermosetting plastic, such as epoxy, polyester resin, vinylester, or other thermoplastic.

In one embodiment, the glass fibers in the fiberglass can be made of various types of glass. In one embodiment, the glass fibers in the fiberglass comprise silica or silicate, with varying amounts of oxides of one or more of calcium, magnesium, or boron. Fiberglass can be a strong lightweight material. Although it is not as strong and stiff as composites based on carbon fiber, it is less brittle, and its raw materials are much cheaper. In one embodiment, the bulk strength and weight of the fiberglass is better than many metals, and it can be more readily molded into complex shapes and provide excellent structural support for the coalescer.

Figure 7:
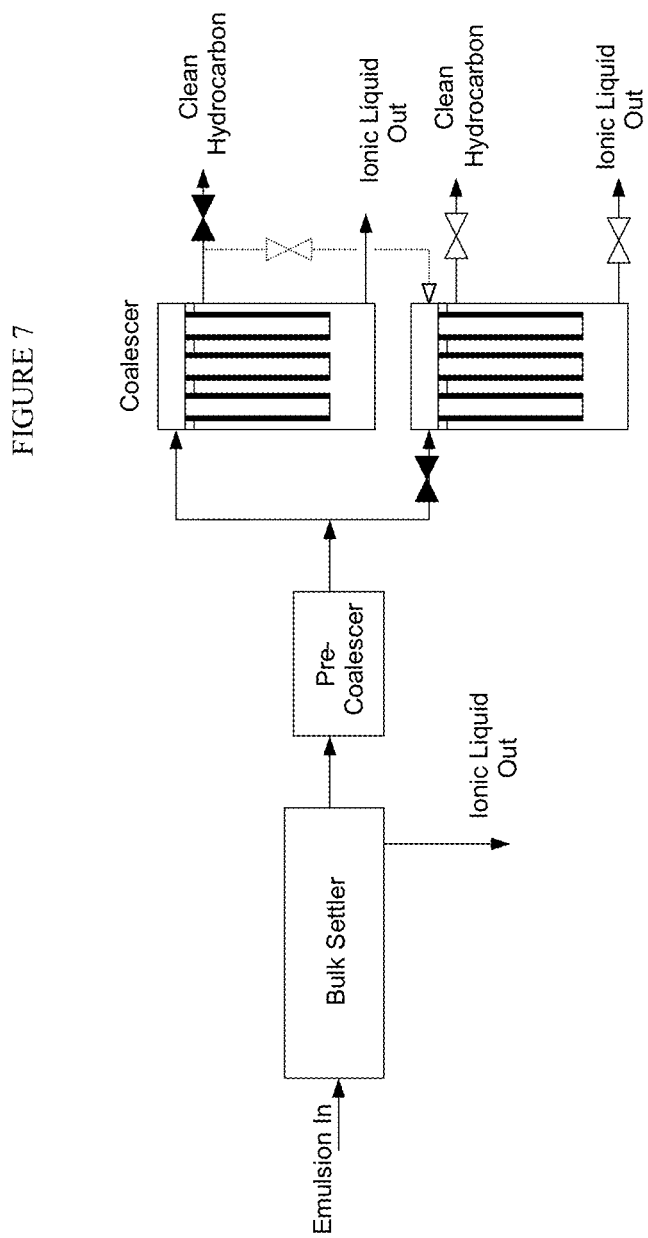
FIG. 7 is a diagram of an alternative integrated coalescing system for separating an ionic liquid from a liquid hydrocarbon.

In one embodiment, the integrated coalescing system comprises two or more coalescers that are fluidly connected to the at least one pre-coalescer. In a sub-embodiment, the two or more coalescers can be arranged in a lead-lag configuration. The lead-lag configuration allows continuous operation when one of the coalescers is serviced or replaced. A lead-lag configuration of the coalescers, when used, ensures superior performance of the integrated system in separating the dispersed ionic liquid from the liquid hydrocarbon, even when there are defects in any one of the coalescers. A lead-lag configuration of the coalescers also helps to extend the life of coalescer cartridges comprising the one or more layers of media. A lead-lag configuration of two coalescers in the integrated coalescing system is shown in FIG. 7.

EXAMPLES

Example 1: Ionic Liquid Droplet Size Distribution in Hydrocarbon-Ionic Liquid Emulsion with 10 Vol % of Ionic Liquid In a cold flow unit, a mixture of ionic liquid and heptane was circulated through a Venturi nozzle by a circulation gear pump under ambient temperature and pressure producing an ionic liquid-heptane emulsion. The mixture contained about 10 vol % of ionic liquid and 90 vol % of heptane. The flow rate through the circulation pump was 2 GPM (0.454 m$^3$/hr) and the pressure drop across the nozzle was 25 psi (172 kPa). Under these conditions, a stable ionic liquid-heptane emulsion was produced, which, if left alone, could take greater than 8-12 hours to separate naturally by gravity into a crystal clear layer of a heptane phase on the top and an ionic liquid phase on the bottom.

Figure 1:
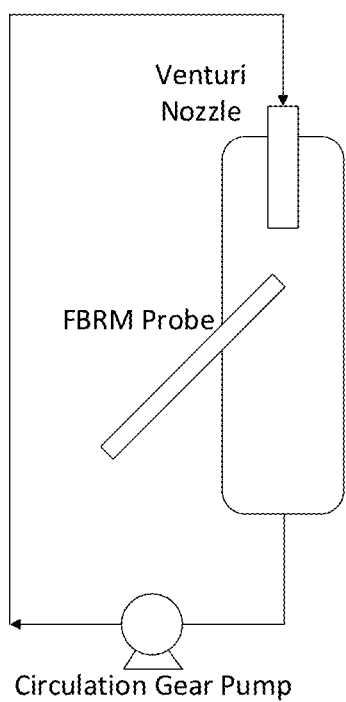
FIG. 1 is a diagram of an experimental cold flow unit used to measure droplet sizes.

To accurately quantify the droplet size distribution of this ionic liquid-heptane emulsion in this cold flow unit, a Focused Beam Reflectance Measurement (FBRM) probe manufactured by Mettler-Toledo was used. As shown in FIG. 1, the probe was installed at a 45° angle with the top measuring window inserted beneath the Venturi nozzle.

Figure 2:
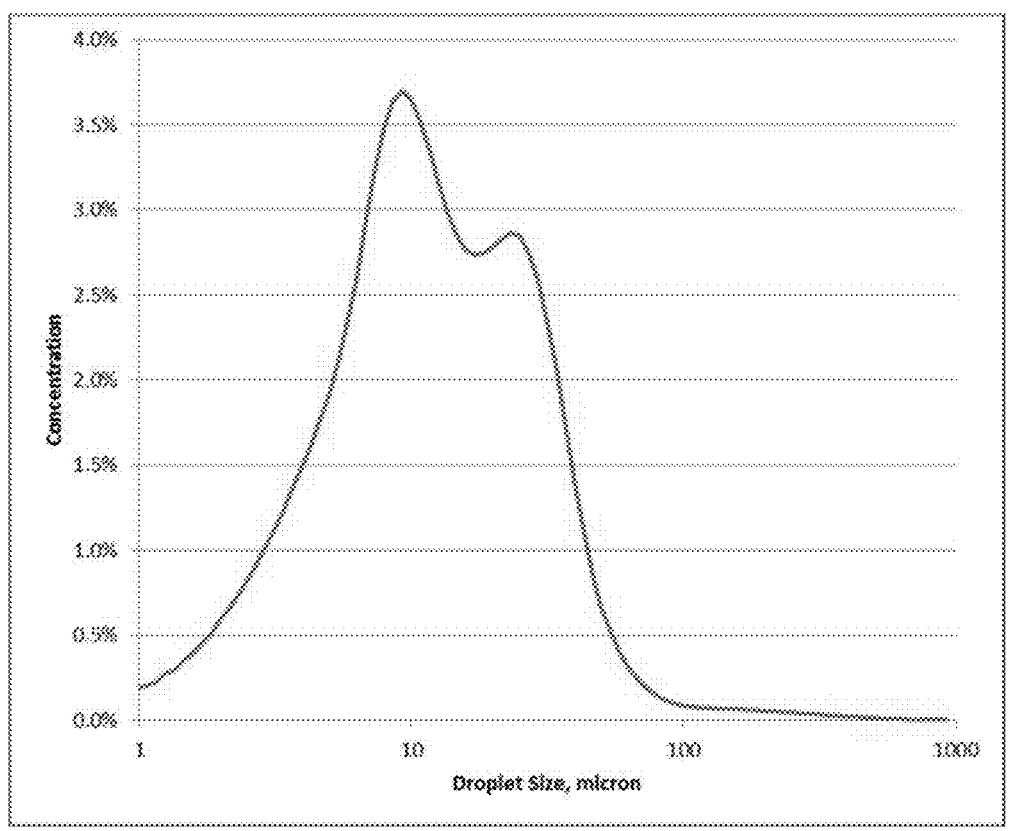
FIG. 2 is a graph of the droplet size distribution in a stable ionic liquid-heptane emulsion comprising 10 vol % ionic liquid.

The ionic liquid droplet size distribution, expressed as number percent concentration versus droplet size, was measured by the FBRM probe as configured in FIG. 1. FIG. 2 shows the ionic liquid droplet size distribution measured by the FBRM probe on the stable ionic liquid-heptane emulsion comprising 10 vol % ionic liquid. As can be seen, there is a wide range of ionic liquid droplets sizes ranging from small sub-micron droplets to large droplets that are greater than 500 microns.

Figure 3:
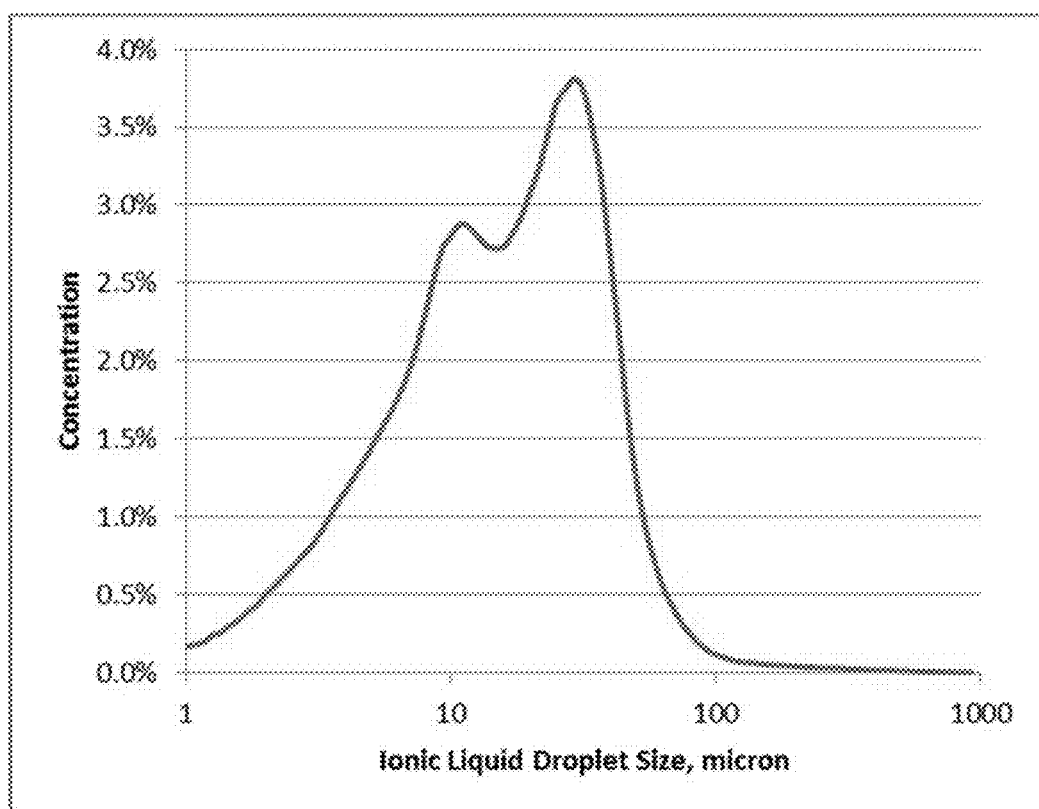
FIG. 3 is a graph of the droplet size distribution in a stable ionic liquid-heptane emulsion comprising 1 vol % ionic liquid.

Example 2: Ionic Liquid Droplet Size Distribution in Hydrocarbon-Ionic Liquid Emulsion with 1 Vol % of Ionic Liquid In the same cold flow unit as described in Example 1, a mixture containing 1 vol % ionic liquid and 99 vol % of heptane was emulsified by circulating the mixture through the Venturi nozzle. The cold flow unit was operated at a pump flow rate of 2 GPM (0.454 m$^3$/hr), and the pressure drop across the Venturi nozzle was 11 psi (76 kPa). When the cold flow unit operation reached a steady state, the ionic liquid droplet size distribution in the emulsion was measured by the FBRM probe. FIG. 3 shows the ionic liquid droplet size distribution that was measured by the FBRM probe on the stable ionic liquid-heptane emulsion comprising 1 vol % ionic liquid. Comparing the droplet size distribution to the results obtained in Example 1, it can be seen that while the overall shape of the droplet size distribution was appreciably different, the distribution still clearly showed a wide range of ionic liquid droplet sizes, again ranging from small sub-micron droplets to large droplets that are greater than 500 microns.

Example 3: Polyamide-Stainless Steel Coalescer for Hydrocarbon-Ionic Liquid Emulsion Separation (Comparative)

Figure 4:
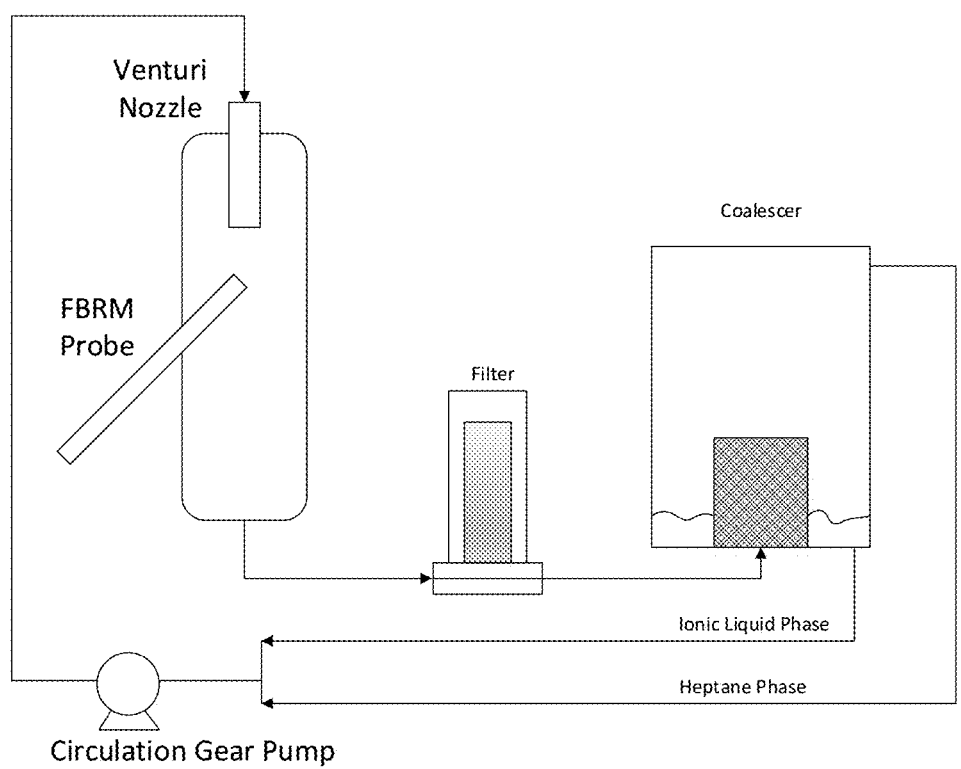
FIG. 4 is a diagram of a second experimental cold flow unit with a pre-coalescer and a coalescer that was used to assess the effectiveness of the separating process and to measure droplet sizes.

A slightly different cold flow unit was designed and tested. The design of this cold flow unit is shown in FIG. 4. This cold flow unit included a pre-coalescer that was a filter and used also included a coalescer with a cartridge made of multiple alternating layers of media including polyamide fabric and stainless steel mesh. This cold flow unit was tested to assess its ability to separate the emulsion produced earlier in Example 2. As shown in FIG. 4, the ionic liquid-heptane emulsion produced by the Venturi nozzle was first introduced to a pre-coalescer having a filter with a filter pore size of 10 microns and then passed to a vertically oriented coalescer. The polyamide fabric used in the coalescer had a relatively large pore size, estimated to be greater than 100 microns. In the coalescer, as ionic liquid droplets passed through the coalescer cartridge's multiple layer media, they coalesced to form larger droplets and settled down on the bottom of the coalescer. After separation, the ionic liquid phase on the bottom of the coalescer and the heptane phase on the top of the coalescer were circulated back to the pump forming a circulation loop.

This cold flow unit was operated at a circulation pump flow rate of 2 GPM (0.454 m$^3$/hr) using a mixture of 1 vol % ionic liquid and 99 vol % heptane and the ionic liquid droplet size distribution in the emulsion produced by the Venturi nozzle was measured by the FBRM probe. The same ionic liquid droplet size distribution that was measured by the FBRM probe on the stable ionic liquid-heptane emulsion comprising 1 vol % ionic liquid described in Example 2 (and shown in FIG. 3) was obtained. The performance of this cold flow unit for producing a clean hydrocarbon stream was then carefully examined by visually observing, without any magnification, the clarity of the heptane phase on the top of the coalescer. After reaching a steady state, the heptane phase remained hazy, indicating that there were still appreciable amounts of unseparated fine ionic liquid droplets remaining in the heptane phase. This cold flow unit, therefore, was not able to completely separate the ionic liquid droplets from the emulsion produced by the Venturi nozzle.

Figure 5:
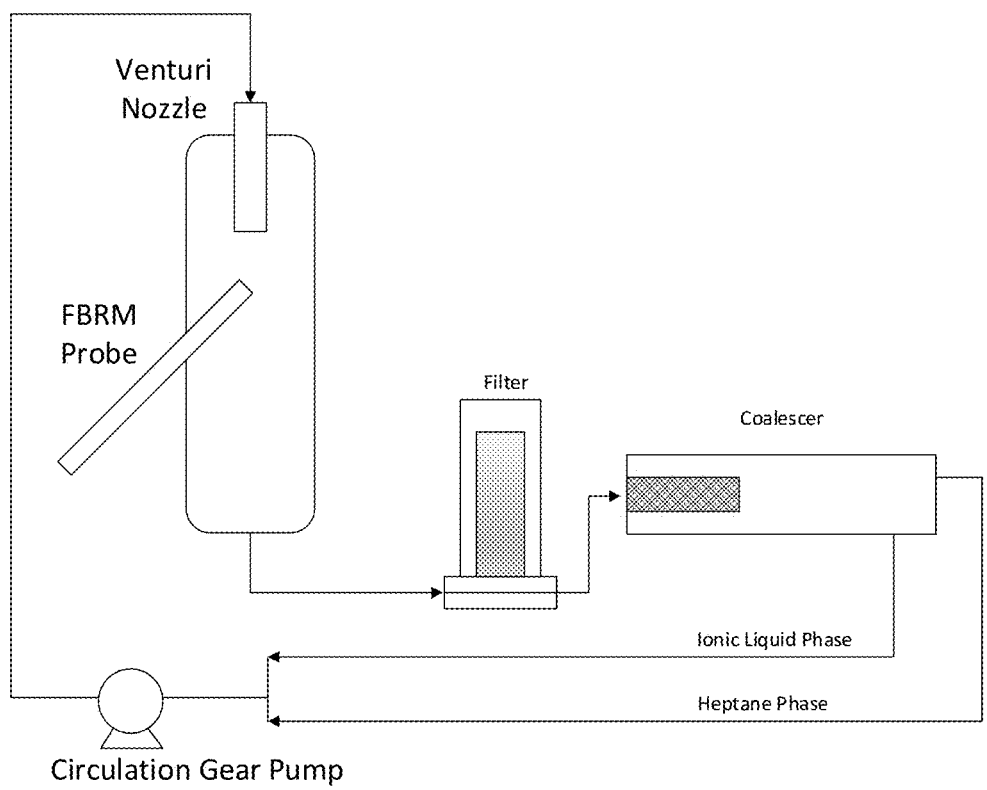
FIG. 5 is a diagram of a third experimental cold flow unit with a pre-coalescer and a coalescer comprising fiberglass media having a fine pore size.

Example 4: Fiberglass-Stainless Steel Coalescer for Hydrocarbon-Ionic Liquid Emulsion Separation, with a Pre-Coalescer Another alternate cold flow unit, as shown in FIG. 5, comprised a pre-coalescer that was a filter, and a coalescer having a coalescer cartridge made of multiple layers of media including a fiberglass fabric and stainless steel mesh. The filter in the pre-coalescer had a filter pore size of 10 microns. The coalescer in this cold flow unit was oriented horizontally. This cold flow unit was tested to separate the emulsion produced in Example 2. In this coalescer cartridge, the fiberglass media was a tightly meshed fabric with a fine pore size in the range of 10 micron.

This cold flow unit was tested to assess its ability to separate the emulsion produced earlier in Example 2. As shown in FIG. 5, the ionic liquid-heptane emulsion produced by the Venturi nozzle was first introduced to a pre-coalescer having a filter with a filter pore size of 10 microns and then passed to the horizontally oriented coalescer. In the coalescer, as ionic liquid droplets passed through the coalescer cartridge's multiple layer media, they coalesced to form larger droplets and settled down on the bottom of the coalescer. After separation, similar to Example 3, the ionic liquid phase on the bottom of the coalescer and the heptane phase on the top of the coalescer were circulated back to the pump forming a circulation loop.

This cold flow unit was operated at a circulation pump flow rate of 2 GPM (0.454 m$^3$/hr) using a mixture of 1 vol % ionic liquid and 99 vol % heptane and the ionic liquid droplet size distribution in the emulsion produced by the Venturi nozzle was measured by the FBRM probe. The same ionic liquid droplet size distribution that was measured by the FBRM probe on the stable ionic liquid-heptane emulsion comprising 1 vol % ionic liquid described in Example 2 (and shown in FIG. 3) was obtained. The performance of this cold flow unit for producing a clean hydrocarbon stream was then carefully examined by visually observing, without any magnification, the clarity of the heptane phase on the top of the coalescer. After reaching a steady state, the heptane phase was crystal clear, with a turbidity of 2.8 NTU, indicating that there was essentially complete separation of the ionic liquid droplets from the emulsion. The amount of ionic liquid remaining in the separated heptane was measured by chemical analysis to be less than 20 ppmv.

Example 5: Fiberglass-Stainless Steel Coalescer for Hydrocarbon-Ionic Liquid Emulsion Separation, without a Pre-Coalescer (Comparative)

To test the impact of the pre-coalescer filter on the separation performance of the cold flow unit, the cold flow testing unit and process described in Example 4 was repeated, but this time, with the pre-coalescer filter bypassed. As in Example 4, the same ionic liquid droplet size distribution that was measured by the FBRM probe on the stable ionic liquid-heptane emulsion comprising 1 vol % ionic liquid described in Example 2 (and shown in FIG. 3)

was obtained. After reaching a steady state, the heptane was hazy, with a turbidity of 11.6, indicating unsatisfactory separation of the ionic liquid from the emulsion. The amount of ionic liquid remaining in the separated heptane in this comparative example was measured to be 40 ppmv by chemical analysis.

Example 6: Integrated Coalescing System with Bulk Settler, Pre-Coalescer, and Fiberglass-Stainless Steel Coalescer for Hydrocarbon-Ionic Liquid Emulsion Separation A pilot plant unit designed for producing alkylate gasoline was used for this example. The pilot plant unit was configured to produce a reactor effluent comprising an emulsion having a dispersed ionic liquid with a wide range of droplet sizes ranging from small droplets less than 20 microns to large droplets greater than 500 microns, with the droplet size distribution being similar to those shown in FIGS. 2 and 3. This pilot plant unit included an integrated coalescing system comprising a bulk settler, a pre-coalescer, and a coalescer. FIG. 6 shows a simplified schematic diagram of this pilot plant unit with the integrated coalescing system. In this pilot plant unit, a reactant mixture containing light hydrocarbon and 2-5 vol % of ionic liquid was circulated around a reactor loop consisted of a Venturi nozzle, an alkylation reactor vessel, a circulation pump, and a heat exchanger. A stable hydrocarbon-ionic liquid emulsion formed in the alkylation reactor, and this emulsion was highly effective at performing the desired alkylation reaction. The reactor effluent remained a stable hydrocarbon-ionic liquid emulsion.

To separate the ionic liquid from the hydrocarbon-ionic liquid emulsion, the reactor effluent was first introduced to a bulk settler containing a coarse coalescing pad that allowed over 90 vol % of large ionic liquid droplets to settle down by gravity. The residence time in the bulk settler was less than 10 minutes. The settling was done effectively in this bulk settler with the coarse coalescing pad using gravity, and the settling produced a clean ionic liquid stream essentially free of hydrocarbon and a raw hydrocarbon stream. The raw hydrocarbon phase from this settler still contained a substantial amount of the ionic liquid, entrained as droplets. The raw hydrocarbon stream was a separated liquid hydrocarbon phase comprising retained ionic liquid droplets. This separated liquid hydrocarbon phase from the settler was then introduced to a pre-coalescer comprising a fiberglass-based filter with a filter pore size of 6-10 micron. This pre-coalescer removed solid particulates that could have fouled the downstream coalescer. This pre-coalescer also functioned as a preconditioner that enabled much more efficient separation in the downstream coalescer. The effluent from the pre-coalescer flowed directly to the coalescer.

In the coalescer in this pilot plant unit, the coalescer cartridge contained multiple alternating layers of tight fiberglass media, in the form of fabrics having fine pore sizes around 10 micron, and stainless steel mesh. The coalescer was highly effective at completely separating essentially all of the ionic liquid droplets from the hydrocarbon phase. The obtained clean hydrocarbon stream was then sent to a series of distillation columns for further separation, while the ionic liquid streams recovered from the emulsion from both the bulk settler and the coalescer were sent to and collected in an ionic liquid reservoir before the ionic liquid in the reservoir was recycled back to the reactor.

The clean ionic liquid phases that were separated in both the bulk settler and the coalescer were sent to an ionic liquid reservoir and circulated back to the alkylation reactor vessel. No observable solid particles formed in any of the clean ionic liquid streams or the clean hydrocarbon stream in this pilot plant unit.

This pilot plant unit with the integrated coalescing system successfully produced crystal clear hydrocarbon effluent from the top of the coalescer and achieved reliable operation for an extended period. This integrated coalescing system would be expected to operate reliably over several years. The amount of the ionic liquid remaining in the clean hydrocarbon stream, which was sent to the series of distillation columns, was estimated to be from zero to 10 ppmv during the entire operation of this pilot plant unit, once it reached a steady state.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible subgeneric combinations of the listed components and mixtures thereof.

The invention illustratively disclosed herein suitably may be practiced in the absence of any element which is not specifically disclosed herein.

It is claimed:

1. A process for separating an ionic liquid from a liquid hydrocarbon, comprising:
   a. settling an emulsion of the ionic liquid and the liquid hydrocarbon, wherein the emulsion comprises a dispersed ionic liquid with a wide range of droplet sizes, ranging from small droplets less than 20 microns to large droplets greater than 500 microns, to separate a clean ionic liquid phase that is free of the liquid hydrocarbon from a separated liquid hydrocarbon phase comprising retained ionic liquid droplets;

b. pre-coalescing the separated liquid hydrocarbon phase in at least one pre-coalescer that removes any particles and begins to form coalesced droplets of the dispersed ionic liquid;

c. coalescing an effluent from the at least one pre-coalescer in at least one coalescer comprising multiple layers of media having a fine pore size of 20 microns or less to produce a clean hydrocarbon stream that is essentially free of the dispersed ionic liquid and produces additional amounts of the clean ionic liquid phase.

2. The process of claim 1, wherein the emulsion comprises the small droplets of the ionic liquid that are less than 10 microns in size.

3. The process of claim 1, wherein the at least one pre-coalescer has a medium with a pore size from 1 to 25 microns.

4. The process of claim 1, wherein the multiple layers of media are arranged to have alternating hydrophilic surface properties and hydrophobic surface properties.

5. The process of claim 1, wherein the multiple layers of media comprise a hydrophobic media comprising an engineered polymer.

6. The process of claim 5, wherein the multiple layers of media additionally comprise a hydrophilic media comprising a metal.

7. The process of claim 6, wherein the metal is a high alloy metal.

8. The process of claim 1, wherein the multiple layers of media comprise a hydrophobic media having the fine pore size of 10 microns or less that coalesces droplets in the emulsion and produces the clean hydrocarbon stream.

9. The process of claim 1, additionally comprising feeding the clean ionic liquid phase to an inlet of a hydrocarbon conversion reactor.

10. The process of claim 1, wherein the settling is done in at least one bulk settler using gravity.

11. The process of claim 10, wherein the emulsion remains in the at least one bulk settler for 0.10 to 10 hours.

12. The process of claim 1, wherein the clean ionic liquid phase contains a majority of an introduced ionic liquid that is fed to a hydrocarbon conversion reactor that produces the emulsion.

13. The process of claim 1, wherein the clean hydrocarbon stream comprises from zero to 20 ppmv of the dispersed ionic liquid.

14. The process of claim 1, wherein the clean hydrocarbon stream has a turbidity from 0.1 to less than 5 NTU.

* * * * *